United States Patent [19]

Henne et al.

[11] Patent Number: 4,522,693
[45] Date of Patent: Jun. 11, 1985

[54] PHOTOPOLYMERIZABLE COMPOSITION WITH ACYLPHOSPHINE SULFIDE PHOTOINITIATOR AND METHOD

[75] Inventors: Andreas Henne, Ludwigshafen; Anton Hesse, Luetzelsachsen; Guenter Heil, Ludwigshafen; Gunnar Schornick, Neuleiningen, all of Fed. Rep. of Germany

[73] Assignee: BASF Aktiengesellschaft, Rheinland-Pfalz, Fed. Rep. of Germany

[21] Appl. No.: 500,429

[22] Filed: Jun. 2, 1983

Related U.S. Application Data

[63] Continuation of Ser. No. 296,895, Aug. 27, 1981, abandoned.

[30] Foreign Application Priority Data

Sep. 15, 1980 [DE] Fed. Rep. of Germany ....... 3034697

[51] Int. Cl.³ .............................................. C08F 2/50
[52] U.S. Cl. .......................... 204/159.15; 204/159.18; 204/159.24; 430/910; 430/921; 546/21; 548/412; 549/5; 549/6; 549/216; 568/15
[58] Field of Search ................... 204/159.24, 159.19, 204/159.15

[56] References Cited

U.S. PATENT DOCUMENTS

3,399,213  8/1968  Osborne .................... 260/326 E

FOREIGN PATENT DOCUMENTS

2909994  2/1980  Fed. Rep. of Germany .
1156460  6/1969  United Kingdom .
1304112  1/1973  United Kingdom .
1406467  9/1975  United Kingdom .

OTHER PUBLICATIONS

"Spectroscopic", Osaki et al., Bull. Chem. Soc., Japan 1973, 46(6), 1803–1806.
Calvert et al., "Photo Chemistry", Wiley & Sons 1966, pp. 488–492.

Primary Examiner—Melvyn I. Marquis
Assistant Examiner—A. H. Koeckert
Attorney, Agent, or Firm—Keil & Weinkauf

[57] ABSTRACT

Acylphosphine sulfides of the formula

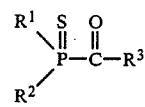

where $R^1$ is alkyl, cycloalkyl or an unsubstituted or substituted phenyl, naphthyl or heterocyclic radical; $R^2$ has the meaning of $R^1$ and can be identical to or different from $R^1$, or is alkoxy, unsubstituted or substituted phenoxy or phenoxyalkyl, or $R^1$ or $R^2$ are linked together to form a ring, which may contain further alkyl substituents and fused-on benzene rings; $R^3$ is alkyl, a cycloaliphatic radical, substituted phenyl, an unsubstituted or substituted naphthyl or heterocyclic radical or the group

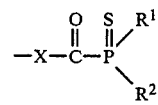

where X is unsubstituted or substituted phenylene or an aliphatic or cycloaliphatic divalent radical; and where one or more of $R^1$, $R^2$ and $R^3$ may be olefinically unsaturated.

These acylphosphine sulfides can be prepared from acylphosphines and sulfur and can be used as photoinitiators in photopolymerizable compositions.

13 Claims, No Drawings

PHOTOPOLYMERIZABLE COMPOSITION WITH ACYLPHOSPHINE SULFIDE PHOTOINITIATOR AND METHOD

This is a continuation of Ser. No. 296,895 filed Aug. 27, 1981, and now abandoned.

The present invention relates to novel acylphosphine sulfides, a process for their preparation and their use as photoinitiators in photopolymerizable compositions such as coating agents, finishes, printing inks, unsaturated polyester molding materials and recording materials.

A number of photoinitiators with different structures are already known, e.g. benzil dimethyl ketal (German Published Application DAS No. 2,261,383), benzoin ethers (German Published Application DAS No. 1,694,149) and thioxanthones (German Laid-Open Application DOS No. 2,003,132). However, photopolymerizable compositions which are hardened using such initiator systems yellow in an undesirable manner, so that these systems cannot be used on light-colored (or white) surfaces or for hardening translucent moldings. The finished sensitized resin mixtures have the further disadvantage of a frequently inadequate storage stability of only a few days, even in the dark. There is also a need for photoinitiators which effect hardening more rapidly than the known systems above.

German Laid-Open Application DOS No. 2,830,927 has also already disclosed acylphosphine oxides and their use as photoinitiators.

It is an object of the present invention to provide compounds which absorb at still longer wavelengths and are suitable as photoinitiators which allow less dangerous light sources to be used or hardening to be carried out with sunlight.

We have found that this object is achieved by providing acylphosphine sulfides of the general formula

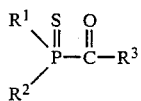   (I)

where $R^1$ is straight-chain or branched alkyl of 1 to 6 carbon atoms, cyclohexyl or cyclopentyl, or a phenyl, naphthyl or O—, S— or N—containing 5- or 6-membered heterocyclic radical which is unsubstituted or substituted by fluorine, chlorine, bromine, $C_1$-$C_4$—alkyl or $C_1$-$C_4$—alkoxy; $R^2$ has the meanings of $R^1$ and can be identical to or different from $R^1$, or is alkoxy of 1 to 6 carbon atoms, phenoxy which is unsubstituted or substituted by chlorine, $C_1$-$C_6$—alkyl or $C_1$-$C_6$—alkoxy, or phenoxyalkyl, where alkyl is of 1 to 4 carbon atoms, or $R^1$ and $R^2$ are linked together to form a ring of 4 to 10 carbon atoms which is unsubstituted or can contain 1 to 6 further alkyl substituents, each of 1 to 4 carbon atoms, as well as 1 or 2 fused-on benzene rings; $R^3$ is straight-chain or branched alkyl of 2 to 18 carbon atoms, a cycloaliphatic radical of 3 to 12 carbon atoms, mono-, di-, tri- or tetra-substituted phenyl or an unsubstituted or mono-, di-, tri- or tetra-substituted naphthyl or O—, S— or N—containing 5- or 6-membered heterocyclic radical, where the substituents can be identical or different and can be alkyl, alkylthio or alkoxy of 1 to 6 carbon atoms or chlorine, bromine or fluorine, or the group

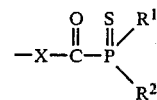

where $R^1$ and $R^2$ have the above meanings and X is unsubstituted or mono-, di-, tri- or tetra-substituted phenylene, where the substituents can be identical or different and can be alkyl, alkylthio or alkoxy of 1 to 6 carbon atoms or halogen with an atomic weight of not more than 80, or X is an aliphatic or cycloaliphatic divalent radical of 2 to 6 carbon atoms; and where one or more of $R^1$, $R^2$ and $R^3$ may be olefinically unsaturated.

The present invention also relates to a process for the preparation of these acylphosphine sulfides, which comprises reacting acylphosphines of the general formula (II)

where $R^1$, $R^2$ and $R^3$ have the above meanings, with elementary sulfur at from 20° to 200° C., preferably from 60° to 120° C., in the presence or absence of an inert solvent and in an inert gas atmosphere.

The present invention furthermore relates to the use of the acylphosphine sulfides of the general formula (I), where $R^3$ can additionally be methyl or phenyl, as photoinitiators in photopolymerizable compositions, for example for coating agents, finishes, printing inks and for the production of plastic moldings based on unsaturated polyester resins, where relevant in combination with secondary or tertiary amines, other photoinitiators or initiators for thermal polymerization.

Acylphosphine sulfides of the general formula (I) in which $R^3$ is a tertiary aliphatic radical are preferred. Especially preferred compounds are those where $R^3$ is phenyl, pyridyl, pyrrolyl, furyl or thienyl which is not less than disubstituted and carries, at least on the two carbon atoms adjacent to the linkage to the carbonyl group, the substituents A and B, which can be identical or different and are alkyl, alkoxy or alkylthio of 1 to 6 carbon atoms, cycloalkyl of 3 to 7 carbon atoms, phenyl or halogen, preferably chlorine or bromine, or $R^3$ is α-naphthyl which is substituted by A and B at least in the 2,8-positions, β-naphthyl which is substituted by A and B at least in the 1,3-positions, or the group

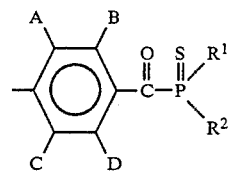

where A, B, C and D are identical or different, C and D have the same meanings as A and B, and $R^1$ and $R^2$ have the above meanings and may be olefinically unsaturated.

The specific statements below apply to the general formula (I) for the acylphosphine sulfides according to the invention:

$R^1$ can be straight-chain or branched alkyl of 1 to 6C atoms, e.g. methyl, ethyl, i-propyl, n-propyl, n-butyl, sec.-butyl, iso-butyl, t-butyl, amyl or n-hexyl; cyclopentyl or cyclohexyl; phenyl or naphthyl; fluorine-, chlorine- or bromine-substituted phenyl or naphthyl, such as monochlorophenyl or dichlorophenyl, $C_1$–$C_4$—alkyl-substituted phenyl or naphthyl, e.g. methylphenyl, ethylphenyl, isopropylphenyl, tert.-butylphenyl, dimethylphenyl or trimethylphenyl, $C_1$–$C_4$—alkoxy-substituted phenyl or naphthyl, e.g. methoxyphenyl, ethoxyphenyl or dimethoxyphenyl, or an O—, S— or N—containing 5- or 6-membered heterocyclic radical, e.g. furyl, thienyl, pyridyl or pyrrolyl, which can likewise be substituted by fluorine, chlorine, bromine, $C_1$–$C_4$—alkyl or $C_1$–$C_4$—alkoxy, e.g. methylfuryl or chloropyridyl.

$R^2$ has the meanings of $R^1$ and can be identical to or different from $R^1$, or is alkoxy of 1 to 6 carbon atoms, phenoxy, which is unsubstituted or substituted by chlorine, $C_1$–$C_6$—alkyl or $C_1$–$C_6$—alkoxy, or phenoxyalkyl where alkyl is of 1 to 4 carbon atoms. Finally, $R^1$ and $R^2$ can be linked together to form a phosphorus-containing ring of 4 to 10 carbon atoms, which can be unsubstituted or contain 1–6 further alkyl substituents, each of 1 to 4 carbon atoms, as well as 1 or 2 fused-on benzene rings.

$R^3$ can be straight-chain or branched alkyl of 2 to 18 carbon atoms, e.g. ethyl, i-propyl, n-propyl, n-butyl, i-butyl, i-amyl, n-hexyl, heptyl, n-octyl, 2-ethylhexyl, i-nonyl, dimethylheptyl, dimethyloctyl, dimethylnonyl, dimethyldecyl, lauryl or stearyl, a cycloaliphatic radical of 3 to 12 carbon atoms, e.g. cyclopropyl, cyclobutyl, cyclpentyl, cyclohexyl, norbornenyl or adamantyl, or a phenyl, naphthyl or O—, S— or N—containing 5- or 6-membered heterocyclic radical which is unsubstituted or mono-, di-, tri- or tetra-substituted by alkyl, alkylthio or alkoxy of 1 to 6 carbon atoms or by chlorine, bromine or fluorine, e.g. methylphenyl, dimethylphenyl, trimethylphenyl, tert.-butylphenyl, isopropylphenyl, methoxyphenyl, dimethoxyphenyl, i-propoxyphenyl, methylthiophenyl, α- or β-naphthyl, thienyl or pyridyl.

$R^3$ can preferably be t-butyl, 1-methylcyclohexyl, 1-methylcyclopentyl or 1,1-dimethyloctyl.

Particularly preferred meanings of $R^3$ are 2,6-dimethylphenyl, 2,6-dimethoxyphenyl, 2,6-dichlorophenyl, 2,6-dibromophenyl, 2-chloro-6-methoxyphenyl, 2-chloro-6-methylthiophenyl, 2,4,6-trimethylphenyl, 2,4,6-trimethoxyphenyl, 2,3,4,6-tetramethylphenyl, 2,6-dimethyl-4-tert.-butylphenyl, 1,3-dimethylnaphth-2-yl, 2,8-dimethylnaphth-1-yl, 1,3-dimethoxy-naphth-2-yl, 1,3-dichloronaphth-2-yl, 2,8-dimethoxynaphth-1-yl, 2,4,6-trimethylpyrid-3-yl, 2,4-dimethoxy-fur-3-yl or 2,4,5-trimethylthiophen-3-yl.

$R^1$, $R^2$ and $R^3$ can also contain C—C double bonds, which enable the photoinitiator to be copolymerized into the binder.

Examples of the acylphosphine sulfides according to the invention are: isobutyroyl-diphenylphosphine sulfide, 2-ethylhexanoyl-diphenylphosphine sulfide, p-toluyl-diphenylphosphine sulfide, o-toluyl-diphenylphosphine sulfide, p-tert.-butylbenzoyldiphenylphosphine sulfide, 3-pyridylcarbonyl-diphenylphosphine sulfide, acryloyldiphenylphosphine sulfide, benzoyl-diphenylphosphine sulfide, terephthaloyl-bis-(diphenylphosphine sulfide), adipoyl-bis-(diphenylphosphine sulfide) and, preferably, pivaloyl-diphenylphosphine sulfide, 1-methyl-1-cyclohexanecarbonyl-bis-(p-tolyl)phosphine sulfide, 2,2-dimethylheptanoyl-diphenylphosphine sulfide and, preferably, 2,6-dimethylbenzoyl-diphenylphosphine sulfide, 2,6-dimethoxybenzoyl-diphenylphosphine sulfide, 2,4,6-trimethylbenzoyl-diphenylphosphine sulfide, 2,3,6-trimethylbenzoyl-diphenylphosphine sulfide, 2,4,6-trimethoxybenzoyl-diphenylphosphine sulfide, 2,6-dichlorobenzoyl-diphenylphosphine sulfide, 2-chloro-6-methylthio-benzoyl-diphenylphosphine sulfide, 2,6-bis-(methylthio)-benzoyl-diphenylphosphine sulfide, 2,3,4,6-tetramethyl-benzoyl-diphenylphosphine sulfide, 2-phenyl-6-methyl-benzoyl-diphenylphosphine sulfide, 1,3-dimethylnaphthalene-2-carbonyl-diphenylphosphine sulfide, 2,8-dimethylnaphthalene-1-carbonyl-diphenylphosphine sulfide, 1,3-dimethoxynaphthalene-2-carbonyl-diphenylphosphine sulfide, 1,3-dichloronaphthalene-2-carbonyl-diphenylphosphine, sulfide, 2,4,6-trimethylpyridine-3-carbonyldiphenylphosphine sulfide, 2,4-dimethylfuran-3-carbonyldiphenylphosphine sulfide, 2,4-dimethoxyfuran-3-carbonyl-bis-(n-butyl)-phosphine sulfide, 2,4,5-trimethyl-thiophene-3-carbonyl-diphenylphosphine sulfide, 2,6-dimethoxybenzoyl-bis-(o-tolyl)-phosphine sulfide, 2,4,6-trimethoxybenzoyl-bis-(p-tolyl)-phosphine sulfide, 2,6-dimethoxybenzoyl-bis-(p-chlorophenyl)-phosphine sulfide, 2,4,6-trimethoxybenzoyl-bis-(p-chlorophenyl)-phosphine sulfide, 2,6-dimethoxybenzoyl-bis-(tert.-butyl)-phosphine sulfide, 2,4,6-trimethoxybenzoyl-bis-(tert.-butyl)-phosphine sulfide and 2,3,5,6-tetrachloroterephthaloyl-bis-(diphenylphosphine sulfide).

The compounds according to the invention can preferably be prepared by reacting an acylphosphine of the formula (II)

with about the equimolar amount of elementary sulfur, in undiluted form or in the presence of a suitable inert organic solvent, in an inert gas atmosphere of, preferably, nitrogen, argon or carbon dioxide, at from 20° to 200° C., preferably at from 60° to 120° C. Preferred solvents are hydrocarbons, such as toluene, cyclohexane and chlorobenzene, and aliphatic and aromatic ethers, such as dibutyl ether, dioxane, diethylene glycol dimethyl ether or diphenyl ether. The resulting solution of the acylphosphine is separated off from any sulfur present by filtration, the solvent is evaporated off from the filtrate and the acylphosphine sulfide which remains as the residue can be further purified by distillation or recrystallization. The process of preparation can be described by way of example as follows:

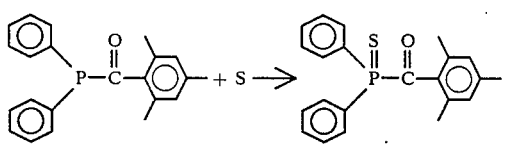

The acylphosphines are obtained by processes which the skilled worker knows from the literature (cf. for example, H. Kunzek, J. Organometallic Chemistry, 49, (1973) 149 and K. Issleib and O. Löw, Zeitschr. f. Anorganische und Analytische Chemie 346, (1966) 241).

The particularly preferred acylphosphine sulfides can also be prepared in the manner described above from the corresponding acylphosphines where $R^3$ is phenyl, pyridyl, pyrrolyl, furyl or thienyl which is not less than disubstituted and carries, at least on the two carbon atoms adjacent to the linkage to the carbonyl group, the substituents A and B, which have the above meanings, or where $R^3$ is α-naphthyl which is substituted by A and B at least in the 2,8-positions, β-naphthyl which is substituted by A and B at least in the 1,3-positions, or the group

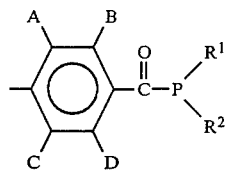

where A, B, C and D are identical or different and have the meanings of A and B above. The preparation of these compounds is described, for example, in German Patent Application No. P 30 20 092.1.

Examples of suitable acylphosphines are: benzoyldiphenylphosphine, p-toluyldiphenylphosphine, o-toluyldiphenylphosphine and p-dimethylaminobenzoyldiphenylphosphine.

Examples of acylphosphines which are suitable for the preparation of the preferred acylphosphine sulfides are: pivaloyldiphenylphosphine, 2,2-dimethylheptanoylditolylphosphine and 2-methyl-2-ethylhexanoyldiphenylphosphine.

Examples of acylphosphines which are suitable for the preparation of the particularly preferred acylphosphine sulfides are: 2,6-dimethylbenzoyldiphenylphosphine, 2,4,6-trimethylbenzoyldiphenylphosphine, 2,6-dimethoxybenzoyldiphenylphosphine and 2,6-dichlorobenzoyldiphenylphosphine.

The Table below gives particular examples of the compounds according to the invention, without this list being regarded as a restriction:

TABLE 1

| (Ph = phenyl) Compound | Melting point °C. | Yield | | Analysis C | H | P | S |
|---|---|---|---|---|---|---|---|
| (structure with CH3, CH3, H3C, CH3 groups) | 108–110° | 52.5% | Calculated Found | 72.53 72.7 | 5.77 5.9 | 8.52 9.0 | 8.79 8.7 |
| (structure with OCH3, OCH3 groups) | 109–111° | 44.5% | Calculated Found | 65.97 65.9 | 4.97 5.0 | 8.12 8.4 | 8.38 7.9 |

The acylphosphine sulfides according to the invention are very reactive as photoinitiators for photopolymerizable monomers having one or more C—C multiple bonds, and mixtures thereof with one another and with known additives, and are particularly suitable photoinitiators in photopolymerizable compositions for coatings, finishes, printing inks and recording materials. They are far superior to the known photoinitiators, for example benzil dimethyl ketal, which is disclosed in German Published Application DAS No. 2,261,383, in respect of yellowing of the resulting finishes and coatings, and they are also particularly advantageous as photoinitiators for photohardening of styrene/polyester resins, which may contain glass fibers and other auxiliaries.

Suitable photopolymerizable monomers are the conventional compounds and substances having polymerizable C—C double bonds which are activated, for example, by aryl, carbonyl, amino, amide, amido, ester, carboxyl or cyanide groups, halogen atoms or additional C—C double or triple bonds, for example vinyl ethers and esters of 3 to 10, preferably 4 to 8, carbon atoms, vinyl-aromatics, such as styrene and vinyltoluene, acrylic and methacrylic acid and esters thereof with mono- or poly-hydric alcohols of up to 20, preferably 1 to 8, carbon atoms, e.g. methyl methacrylate, 2-hydroxyethyl acrylate, 2-hydroxyethyl methacrylate, butane-1,4-diol diacrylate and hexane-1,6-diol diacrylate, nitriles and amides of acrylic or methacrylic acid, maleates and fumarates of alcohols of 1 to 20, preferably 1 to 8, carbon atoms, e.g. diethyl fumarate, N-vinyl compounds, such as N-vinylpyrrolidone, N-vinylcaprolactam and N-vinylcarbazole, and allyl esters, such as diallyl phthalate.

Examples of suitable photopolymerizable compounds of relatively high molecular weight are unsaturated polyesters prepared from α,β-unsaturated dicarboxylic acids, such as maleic, fumaric or itaconic acid, if desired mixed with saturated or aromatic dicarboxylic acids, such as adipic, phthalic or terephthalic acid, by reacting these acids with alkanediols, such as ethylene glycol, propylene glycol, butanediol, neopentylglycol or oxyalkylated bisphenol A; epoxide acrylates prepared from acrylic or methacrylic acid and aromatic or aliphatic diglycidyl ethers, and urethane acrylates (for example prepared from hydroxyalkyl acrylates and polyisocyanates) and polyester acrylates (for example prepared from hydroxyl-containing saturated polyesters and acrylic and methacrylic acid).

Saturated and/or unsaturated polymers and other additives, such as inhibitors against thermal polymerization, paraffin, pigments, dyes, peroxides, leveling agents, fillers and glass fibers, and stabilizers against thermal or photochemical degradation can be added in a conventional manner to the photopolymerizable compounds, the type and amount of additive depending on the particular use. The composition of the above compounds required for a particular use, and mixtures thereof with additives, are familiar to a skilled worker.

The acylphosphine sulfides according to the invention are generally used in these mixtures in a concentration of from 0.01 to 15% by weight, preferably from 0.05 to 5% by weight, based on the photopolymerizable composition. If desired, they can be combined with accelerators which eliminate the inhibitory effect of atmospheric oxygen on the photopolymerization.

Examples of such accelerators or synergistic agents are secondary and/or tertiary amines, such as methyldiethanolamine, dimethylethanolamine, triethylamine triethanolamine, ethyl p-dimethylaminobenzoate, benzyl-dimethylamine, dimethylaminoethyl acrylate, N-phenylglycine and N-methyl-N-phenylglycine, and similar compounds which are known to those skilled in the art. Hardening can also be accelerated by using aliphatic and aromatic halides, such as 2-chloromethylnaphthalene and 1-chloro-2-chloromethylnaphthalene, and, where relevant, agents which form free radicals and are generally used as initiators for thermal polymerization, e.g. peroxides, azo compounds and compounds with a labile carbon-carbon bond, these being added in amounts of up to 15% by weight, based on the photopolymerizable composition, and being known to the skilled worker.

The acylphosphine sulfides can furthermore be used, in the presence or absence of the above synergistic agents and accelerators, in combination with other photoinitiators for photohardening coatings, finishes, printing inks and photosensitive recording materials, for example photopolymerizable printing plates and styrene/polyester resins. Examples of such photoinitiators are aromatic ketones, such as benzil ketals, benzoin ethers, benzoin esters, $C_1$–$C_4$—alkyl—, chloro- or chloromethyl-substituted thioxanones, the acylphosphines described in German Patent Application No. P 30 20 092.1, the acylphosphine oxides and acylphosphinic acid esters disclosed in German Laid-Open Applications DOS No. 2,830,927 and DOS No. 2,909,994, and aromatic disulfides and naphthalenesulfonyl chlorides. These and any other suitable compounds are known to the skilled worker.

Sources of radiation which preferentially emit light in the absorption range of the compounds according to the invention, ie. between 230 and 450 nm, are generally used for triggering off polymerization of the above mixtures. Low-pressure, medium-pressure and high-pressure mercury lamps, superactinic fluorescent tubes and pulsed radiators are particularly suitable. If appropriate, the said lamps can be doped.

A particular advantage of the acylphosphine sulfides according to the invention is that they can be used as photoinitiators for photopolymerization with light sources which have a relatively long wavelength and are therefore less dangerous, such as fluorescent tubes, or for hardening with sunlight.

In the Examples which follow, parts and percentages are by weight, unless otherwise indicated. Parts by volume bear the same relation to parts by weight as the liter to the kilogram.

EXAMPLE 1

7.0 parts of 2,6-dimethoxy-benzoyl-diphenylphosphine (cf. Example 1 of German Patent Application No. P 30 20 092.1) are dissolved in 60 parts by volume of toluene and the solution is flushed with nitrogen for 30 minutes. 0.64 part of sulfur is then added and the solution is stirred under a nitrogen atmosphere at 60° C. for 4 hours and then cooled. The solvent is then stripped off under reduced pressure and the residue is recrystallized from toluene.

Yield: 3.4 parts of 2,6-dimethoxybenzoyl-diphenylphosphine sulfide (44.5% of theory); melting point: 109°–111° C.;

NMR (CDCl$_3$, δ): 3.56 (s, 6H); 6.52 (d, 2H); 7.2–8.2 (m, 11H).

Analysis: $C_{21}H_{19}O_3PS$ (382).

Calculated: C 65.97 H 4.97 P 8.12 S 8.38. Found: C 65.9 H 5.0 P 8.4 S 7.9.

EXAMPLE 2

6.6 parts of 2,4,6-trimethylbenzoyl-diphenylphosphine (cf. Example 2 of German Patent Application No. P 30 20 092.1) are dissolved in 60 parts by volume of toluene and the solution is flushed with nitrogen for 30 minutes. 0.64 part of sulfur is then added and the solution is stirred under a nitrogen atmosphere at 60° C. for 2 hours and then cooled. The solvent is stripped off under reduced pressure and the residue is recrystallized from diethyl ether.

Yield: 3.6 parts of 2,4,6-trimethylbenzoyl-diphenylphosphine sulfide (52.5% of theory); melting point: 108°–110° C., NMR (CDCl$_3$, δ): 1.98 (s, 6H); 2.28 (s, 3H); 6.81 (s, 2H); 7.2–7.8 (m, 6H); 7.8–8.4 (m, 4H).

Analysis: $C_{22}H_{21}OPS$ (364).

Calculated: C 72.53 H 5.77 P 8.52 S 8.79.

Found: C 72.7 H 5.9 P 8.7 S 9.0.

EXAMPLE 3

To measure the hardening activity of the compounds according to the invention, the change in temperature in unsaturated polyester resin (UP resin) during irradiation with UV light is recorded by immersing a thermocouple which is coated with a layer of wax and connected to a temperature recorder (Tastotherm Script 3N, standard thermocouple T 300 from Deutsche Gulton GmbH) in a tin-plate lid which is filled with 10 g of UP resin and has a diameter of 5 cm (thickness of the UP resin: 4.8 mm). The lid is embedded in rigid polyurethane foam in order to avoid heat losses during irradiation with UV light. The radiation source is a UV field from 5 fluorescent tubes (TLAK 40 W/05, Philips) arranged side by side at a distance of 8.5 cm from the surface of the UP resin.

The hardening time $ht_{25° C.-T_{max}}$ and the maximum hardening temperature $T_{max}$ reached are obtained as characteristic parameters of hardening activity from the temperature/time curves recorded. The hardening time $ht_{25° C.-T_{max}}$ is the time taken for the temperature of the sample to rise from 25° C. to $T_{max}$.

The following unsaturated polyester resins were used in the Examples and Comparative Examples:

Resin A is a 65% strength solution of an unsaturated polyester of maleic acid, o-phthalic acid, ethylene glycol and propylene-1,2-glycol in a molar ratio of 1:2:2.3:0.70 in styrene, which is stabilized with 0.01% of hydroquinone. The unsaturated polyester has an acid number of 50.

Resin B is a 66% strength solution of an unsaturated polyester of maleic acid, o-phthalic acid and propylene-1,2-glycol in a molar ratio of 1:0.5:1.5 in styrene, which is stabilized with 0.01% of hydroquinone. The unsaturated polyester has an acid number of 50.

Resin C is a 65% strength solution of an unsaturated polyester of maleic acid, o-phthalic acid, propylene- 1,2-glycol and diethylene glycol in a molar ratio of 1:0.25:1:0.25 in styrene, which is stabilized with 0.012% of hydroquinone. The unsaturated polyester has an acid number of 43.

Resin D is a 67% strength solution of an unsaturated polyester of maleic acid, tetrahydrophthalic acid and diethylene glycol in a molar ratio of 1:0.5:1.5 in styrene, which is stabilized with 0.01% of hydroquinone. The unsaturated polyester has an acid number of 43.

Resin E is a 65% strength solution of an unsaturated polyester of maleic acid, isophthalic acid, propylene-1,2-glycol and diethylene glycol in a molar ratio of 1:0.67:0.72,:1 in styrene, which is stabilized with 0.01% of hydroquinone. The unsaturated polyester has an acid number of 26.

The following compounds of the prior art were used as UV sensitizers in Comparative Examples:
I benzil dimethyl ketal
II benzoin methyl ether
III benzoin isopropyl ether
IV methylolbenzoin methyl ether.

These compounds were compared with the two photoinitiators according to the invention:
V  2,6-dimethoxybenzoyl-diphenylphosphine sulfide and
VI 2,4,6-trimethylbenzoyl-diphenylphosphine sulfide.

The results can be seen from Table 2.

TABLE 2

UV hardening of sensitized UP resins by irradiation with fluorescent tubes

| UP resin | UV Initiator (0.2%) | $h^t 25°$ C.-$T_{max}$ [min/s] | $T_{max}$ [°C.] |
|---|---|---|---|
| A | I | 8/00 | 114 |
| B | I | 9/45 | 119 |
| C | I | 10/15 | 123 |
| D | I | 8/30 | 122 |
| A | II | 23/22 | 104 |
| B | II | 12/07 | 109 |
| C | II | 13/15 | 114 |
| D | II | 11/15 | 108 |
| A | III | 13/22 | 100 |
| B | III | 11/30 | 117 |
| C | III | 11/15 | 123 |
| D | III | 9/08 | 122 |
| A | IV | 7/30 | 107 |
| B | IV | 6/45 | 116 |
| C | IV | 6/38 | 123 |
| D | IV | 5/30 | 123 |
| A | V (0.1%) | 5/08 | 102 |
| B | V (0.2%) | 3/33 | 138 |
| C | V (0.2%) | 3/38 | 148 |
| D | V (0.2%) | 3/20 | 136 |
| E | V (0.2%) | 3/50 | 130 |
| A | VI (0.1%) | 5/54 | 105 |
| B | VI (0.2%) | 4/00 | 135 |
| C | VI (0.2%) | 3/45 | 142 |
| D | VI (0.2%) | 3/40 | 126 |
| E | VI (0.2%) | 4/15 | 130 |

Compared with the commercially available photoinitiators (I–IV), those according to the invention have a significantly higher activity, and the molding yellows less.

EXAMPLE 4

3 parts of photoinitiator are dissolved in a binder comprising 65 parts of a reaction product of bisphenol A glycidyl ether and acrylic acid, and 35 parts of hexane-1,6-diol diacrylate. The finished mixture is knife-coated in a thickness of 60 μm onto glass plates and the latter are passed at a distance of 10 cm below a high-pressure mercury lamp (power: 80 W/cm of arc length).

The reactivity is quoted as the maximum possible conveyor belt speed at which a coating which is sufficiently hardened not to be scratched by a finger-nail can still be obtained. The results are summarized in Table 3.

EXAMPLE 5

3% of methyldiethanolamine are added to a finish prepared as described in Example 4. As in that Example, the finish is then knife-coated onto glass plates and the plates are exposed. According to the results, which are summarized in Table 3, the speed at which the compounds according to the invention effect hardening can be increased by adding an amine accelerator.

TABLE 3

| Photoinitiator | maximum conveyor belt speed in m/minute | | |
|---|---|---|---|
| | in air | under an inert gas | in air, with the addition of 3% of methyldiethanolamine |
| 2,4,6-Trimethylbenzoyl-diphenylphosphine sulfide | <12 | 140 | 24 |
| 2,6-Dimethoxybenzoyl-diphenylphosphine sulfide | <12 | 150 | 24 |

We claim:

1. A process for the preparation of a photopolymerizable composition which comprises: incorporating a photoinitiator into a photopolymerizable composition containing monomers having polymerizable C—C double bonds, said photoinitiator being an acylphosphine sulfide of the formula

where $R^1$ is straight-chain or branched alkyl of 1 to 6 carbon atoms, cyclohexyl or cyclopentyl, or a phenyl, naphthyl or O—, S— or N—containing 5- or 6-membered heterocyclic radical which is unsubstituted or substituted by fluorine, chlorine, bromine, $C_1$-$C_4$—alkyl or $C_1$-$C_4$—alkoxy; $R^2$ has the meanings of $R^1$ and can be identical to or different from $R^1$, or is alkoxy of 1 to 6 carbon atoms, phenoxy which is unsubstituted or substituted by chlorine, $C_1$-$C_6$—alkyl or $C_1$-$C_6$—alkoxy, or phenoxyalkyl, where alkyl is of 1 to 4 carbon atoms, or $R^1$ and $R^2$ are linked together to form a ring of 4 to 10 carbon atoms which is unsubstituted or can contain 1 to 6 further alkyl substituents, each of 1 to 4 carbon atoms, as well as 1 or 2 fused-on benzene rings; $R^3$ is straight-chain or branched alkyl of 2 to 18 carbon atoms, a cycloaliphatic radical of 3 to 12 carbon atoms, mono-, di-, tri- or tetra-substituted phenyl or an unsubstituted or mono-, di-, tri- or tetra-substituted naphthyl, where the substituents can be identical or different and can be alkyl, alkylthio or alkoxy of 1 to 6 carbon atoms or chlorine, bromine or fluorine, or the group

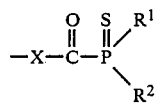

where $R^1$ and $R^2$ have the above meanings and X is unsubstituted or mono-, di-, tri- or tetra-substituted phenylene, where the substituents can be identical or different and can be alkyl, alkylthio or alkoxy of 1 to 6 carbon atoms or halogen of atomic weight of not more than 80, or X is an aliphatic or cycloaliphatic divalent radical of 2 to 6 carbon atoms; and where one or more of $R^1$, $R^2$ and $R^3$ may be olefinically unsaturated, where $R^3$ can also be methyl or phenyl.

2. A process as set forth in claim 1, wherein the composition includes a secondary and/or tertiary amine.

3. A process as set forth in claim 1, wherein the acylphosphine sulfide is used as a photoinitiator, in a photopolymerizable coating agent, finish, printing ink or recording material, in a concentration of 0.01% to 15%.

4. A process as set forth in claim 1, wherein the photopolymerizable composition is used for producing a plastic molding based on an unsaturated polyester resin.

5. A process as set forth in claim 2, wherein the photopolymerizable composition is used for producing a plastic molding based on an unsaturated polyester resin.

6. A process as set forth in claim 1, wherein an acylphosphine sulfide of the general formula (I) is used as the UV sensitizer in combination with a compound from the group consisting benzil ketals, benzoin ethers, benzoin esters, $C_1$-$C_4$—alkyl—, chloro- or chloromethyl-substituted thioxanthones, aromatic disulfides, naphthalenesulfonyl chlorides, acylphosphines, acylphosphine oxides and acylphosphinic acid esters.

7. A process as set forth in claim 1, wherein the acylphosphine sulfide is used in combination with an initiator for thermal polymerization.

8. A process as set forth in claim 2, wherein the acylphosphine sulfide is used in combination with an initiator for thermal polymerization.

9. A process as set forth in claim 4, wherein the acylphosphine sulfide is used in combination with an initiator for thermal polymerization.

10. A process as set forth in claim 5, wherein the acylphosphine sulfide is used in combination with an initiator for thermal polymerization.

11. A process as set forth in claim 6, wherein the acylphosphine sulfide is used in combination with an initiator for thermal polymerization.

12. A photopolymerizable composition comprising monomers having polymerizable C—C double bonds and as a photoinitiator an acylphosphine sulfide of the formula

where $R^1$ is straight-chain or branched alkyl of 1 to 6 carbon atoms, cyclohexyl or cyclopentyl, or a phenyl, naphthyl or O—, S— or N—containing 5- or 6-membered heterocyclic radical which is unsubstituted or substituted by fluorine, chlorine, bromine, $C_1$-$C_4$—alkyl or $C_1$-$C_4$—alkoxy; $R^2$ has the meanings of $R^1$ and can be identical to or different from $R^1$, or is alkoxy of 1 to 6 carbon atoms, phenoxy which is unsubstituted or substituted by chlorine, $C_1$-$C_6$—alkyl or $C_1$-$C_6$—alkoxy, or phenoxyalkyl, where alkyl is of 1 to 4 carbon atoms, or $R^1$ and $R^2$ are linked together to form a ring of 4 to 10 carbon atoms which is unsubstituted or can contain 1 to 6 further alkyl substituents, each of 1 to 4 carbon atoms, as well as 1 or 2 fused-on benzene rings; $R^3$ is straight-chain or branched alkyl of 2 to 18 carbon atoms, a cycloaliphatic radical of 3 to 12 carbon atoms, mono-, di-, tri- or tetra-substituted phenyl or an unsubstituted or mono-, di-, tri- or tetra-substituted naphthyl, where the substituents can be identical or different and can be alkyl, alkylthio or alkoxy of 1 to 6 carbon atoms or chlorine, bromine or fluorine, or the group

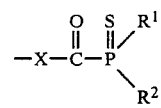

where $R^1$ and $R^2$ have the above meanings and X is unsubstituted or mono-, di-, tri- or tetra-substituted phenylene, where the substituents can be identical or different and can be alkyl, alkylthio or alkoxy of 1 to 6 carbon atoms or halogen of atomic weight of not more than 80, or X is an aliphatic or cycloaliphatic divalent radical of 2 to 6 carbon atoms; and where one or more of $R^1$, $R^2$ and $R^3$ may be olefinically unsaturated, where $R^3$ can also be methyl or phenyl.

13. The composition of claim 12 wherein the photopolymerizable composition comprises an unsaturated polyester resin.

* * * * *